United States Patent
Menzies

(10) Patent No.: US 7,007,517 B2
(45) Date of Patent: Mar. 7, 2006

(54) KNIT SOCK

(75) Inventor: Balfour Stirling Mullins Menzies, Hickory, NC (US)

(73) Assignee: Menzies—Southern Hosiery Mills, Inc., Hickory, NC (US)

(*) Notice: Subject to any disclaimer, the term of this patent is extended or adjusted under 35 U.S.C. 154(b) by 0 days.

(21) Appl. No.: 10/919,974

(22) Filed: Aug. 17, 2004

(65) Prior Publication Data

US 2006/0021389 A1  Feb. 2, 2006

Related U.S. Application Data

(60) Provisional application No. 60/598,152, filed on Aug. 2, 2004.

(51) Int. Cl.
*D04B 9/46* (2006.01)

(52) U.S. Cl. .................................................. 66/185

(58) Field of Classification Search .............. 66/178 R, 66/185, 186, 187, 188

See application file for complete search history.

(56) References Cited

U.S. PATENT DOCUMENTS

| | | | |
|---|---|---|---|
| 4,057,981 A | 11/1977 | Runac | |
| 4,255,949 A | 3/1981 | Thorneburg | |
| 4,898,007 A * | 2/1990 | Dahlgren | 66/185 |
| D386,608 S | 11/1997 | Green | |
| 5,724,836 A | 3/1998 | Green | |
| 6,012,177 A | 1/2000 | Cortinovis | |
| 6,308,337 B1 | 10/2001 | Penley | |
| 6,550,289 B1 | 4/2003 | Higgins | |
| 6,606,750 B1 | 8/2003 | Solwey | |
| 2003/0131635 A1 | 7/2003 | Lynch et al. | |

* cited by examiner

*Primary Examiner*—Danny Worrell
(74) *Attorney, Agent, or Firm*—Summa, Allan & Addition, P.A.

(57) ABSTRACT

A knit sock useful for patients susceptible to foot problems resulting from diabetes or other conditions includes a leg section and a foot section. The leg section has sufficient expandability to be drawn over and cover at least a portion of a leg of a wearer. The foot section includes a heel section, a toe section, a sole section, and an instep section. The instep includes a ventilation panel and a flex zone, each having a different stitch construction. The ventilation panel allows air to pass through the sock and the flex zone prevents bunching or wrinkling of the material against the skin of the foot.

37 Claims, 2 Drawing Sheets

KNIT SOCK

CROSS-REFERENCE TO RELATED APPLICATIONS

This application claims priority from provisional application Ser. No. 60/598,152 filed Aug. 2, 2004 for KNIT SOCK, which is hereby incorporated entirely herein by reference.

FIELD OF THE INVENTION

The present invention relates generally to a knit sock and more particularly to a knit sock useful for patients susceptible to foot problems resulting from diabetes or other medical conditions.

BACKGROUND OF THE INVENTION

Diabetes is a disease in which the body does not produce or properly use insulin. Insulin is a hormone that is needed to convert sugar, starches and other food into energy needed for daily life. The American Diabetes Association estimates that there are over 18 million people in the United States alone, or 6.3% of the population, who have diabetes.

Diabetic neuropathies are a family of nerve disorders caused by diabetes. People with diabetes can, over time, have damage to nerves throughout the body. Neuropathies lead to numbness and sometimes pain and weakness in the hands, arms, feet, and legs. People with diabetes can develop nerve problems at any time, but the longer a person has diabetes, the greater the risk.

Diabetic neuropathies can be classified as peripheral, autonomic, proximal, and focal, each of which affects different parts of the body in different ways. The most common type is peripheral neuropathy, also called distal symmetric neuropathy, which affects the arms and legs. In particular, peripheral neuropathy causes either pain or loss of feeling in the toes, feet, legs, hands, and arms. Blisters and sores may appear on numb areas of the foot, and the loss of sensation in the feet means that such sores or injuries may not be noticed and may become ulcerated or infected. If foot injuries are not treated promptly, the infection may spread to the bone, and the foot may then have to be amputated.

Patients suffering from diabetes are also at increased risk for cardiovascular complications. Diabetes is believed to affect how the heart pumps blood through the body. Diabetes can change the chemical makeup of some of the substances found in the blood, which in turn can cause blood vessels to narrow or to clog up completely. Such circulation problems also increase the risk of foot ulcers, and as a result cardiovascular complications resulting from diabetes is another leading cause of lower-limb amputations in the people with diabetes.

Thus the nature of diabetes can result in nerve damage and/or diminished circulation in the extremities, such as the feet. This, combined with the normally high moisture environment of the foot and the often undesired barrier properties of certain stockings and shoes, and the normal friction created by foot movement (e.g., walking), can increase the problems suffered by such persons.

U.S. Pat. No. 5,724,836 to Green is directed to a sock stated to cushion and at the same time keep the wearer's foot cool and dry. The sock includes a breathable instep panel, a padded sole, and a transition zone located between the foot section and leg section. Despite the potential benefits of the sock, it is not intended for use with diabetic patients. Patients with poor circulation in the extremities can have significant swelling in their feet and legs. It can be difficult to put on and remove a sock like that of the '836 patent from a patient's swollen foot and/or leg region. In addition, a sock like that of the '836 patent can wrinkle or bunch about the foot of the wearer during normal movements and thus can also potentially irritate the skin of the wearer.

BRIEF SUMMARY OF THE INVENTION

The present invention provides a knit sock that can be useful in minimizing and/or preventing various problems associated with poor circulation, nerve damage, and other physical manifestations associated with diabetes. The sock is also useful for patients having health conditions other than diabetes, such as arthritis, that can adversely affect their extremities.

The sock of the present invention can be readily expanded several times its circumference to provide ease and comfort when putting the sock onto the foot and leg of the wearer. Thus the sock can useful for patients suffering swelling in the feet and legs. The sock of the invention can also provide good air ventilation and circulation to help keep the foot of the wearer drier than with conventional socks. Further, the sock is designed to prevent substantial bunching or wrinkling of the sock against the foot of the wearer, for example, when the foot bends in use. The present invention can thus minimize irritation of the skin, which in turn can minimize and help prevent formation of sores or ulcers.

The sock includes a leg section and a foot section. The leg section has substantial circumferential expandability to allow it to be readily drawn over and cover at least a portion of a leg of a wearer. Because the leg section is readily expandable, it can be fitted onto the wearer with relative ease and comfort. This can be particularly useful for diabetic or other patients with circulatory problems with substantial swelling in their extremities. The sock can also remain in place once fitted onto the wearer. An exemplary knit construction useful to impart the desired degree of expansion and fit is a rib knit construction, which optionally includes an elastic yarn.

The foot section of the sock includes a heel section, a toe section, a sole section, and an instep section. The instep section includes at least one ventilation panel and at least one flex zone, each of which has a different knit construction. The ventilation panel is formed of a knit construction designed to allow the passage of air therethrough and to provide ventilation along at least a portion thereof. Advantageously, the ventilation panel has an open knit construction resulting from the presence of tuck stitches interspersed with plain stitches.

The flex zone has a knit construction designed to prevent bunching of the sock against the foot of the wearer as the foot bends in use. To reduce wrinkling or bunching of the fabric, the flex zone is generally formed of a smaller or finer knit construction as compared to the knit structure of the ventilation panel. In addition, the flex zone is generally formed of a less open knit construction as compared to the ventilation zone, such as a single or jersey knit construction.

The relative positions of the ventilation panel and the flex zone along the instep of the sock are selected to provide the desired degree of air flow and reduced bunching or wrinkling of the sock. Generally, the sock includes at least one ventilation panel located between the toe section and an ankle section of the sock covering an ankle joint of the wearer and at least one flex zone located on an upper portion of the instep section between the ankle section and the ventilation panel. In addition, the flex zone extends from one side of the sock from a region near the ankle section across the top of the foot to the opposite side of the sock to the opposing ankle section.

In one embodiment of the invention, the sock includes a flex zone integrally knit to a lower portion of the leg section. In an alternative embodiment of the invention, the sock includes at least a first ventilation panel along an upper portion of the instep section which is integrally knit to a lower portion of the leg section. In this embodiment, the sock also includes at least a second ventilation panel along a lower portion of the instep section and at least one flex zone located along an intermediate portion of the instep section between the first and second ventilation panels.

The sole section of the sock of the invention is constructed to provide a desired degree of padding to cushion and protect the foot to further minimize or prevent irritation of the skin. An exemplary knit construction useful for the sole section is a sandwich plated cushion knit which includes a plurality of terry loops on a surface of the sole section adjacent the foot of the wearer.

The toe section can also be constructed to minimize and prevent irritation of the skin of the wearer. Advantageously, the toe section includes an inverted toe closure seam or flat seam oriented outwardly away from a surface of the sock contacting the skin of a wearer. In addition, the sock of the invention can have a Y heel construction.

The sock can be made using one or more of the types of yarns useful for the production of knit socks, including one or more yarns formed of synthetic or man-made fibers (including blends of different synthetic fibers), one or more yarns formed of natural fibers (including blends of different natural fibers), and one or more yarns formed of blends of synthetic fibers and natural fibers. Yarns having different properties, such as yarns formed of different types of fibers, yarns having different deniers, and the like, can also be used in combination with one another within one or more sections of the sock. For example, one or more sections of the sock can include at least two different yarns, each having a different denier and/or formed of different types of fibers. As a non-limiting example, different sections of the instep of the sock can include a first yarn of acrylic fiber having a first denier and a second yarn of nylon fibers having a second denier different from the first denier of the acrylic yarn. Advantageously, the sock includes yarns having moisture wicking properties, such as acrylic yarns.

BRIEF DESCRIPTION OF THE DRAWINGS

Figure 1:
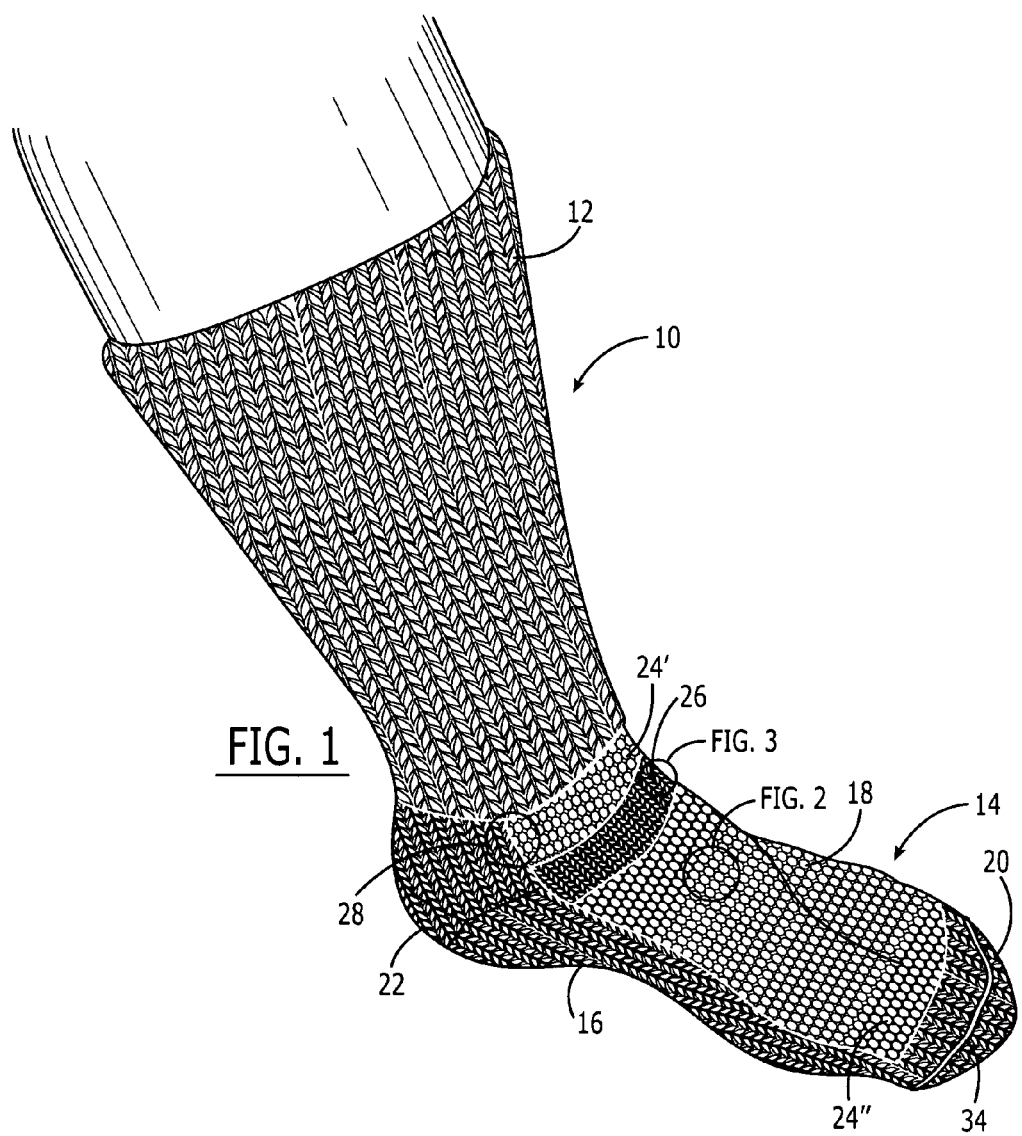
Figure 2:
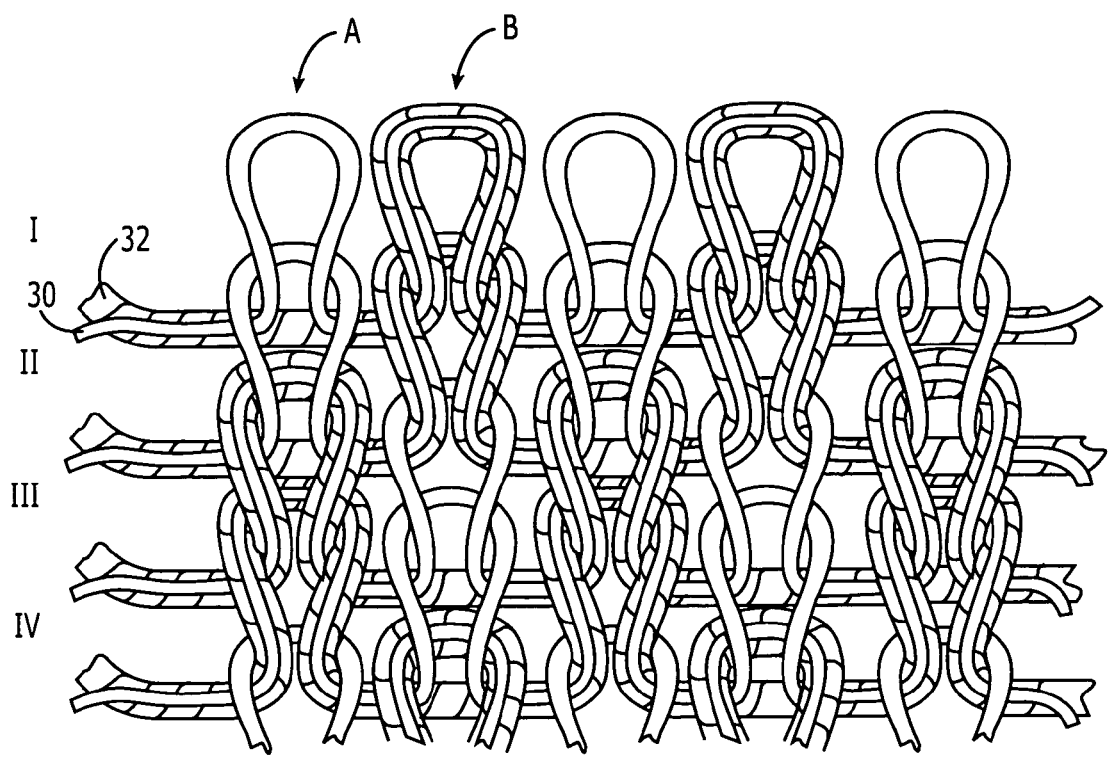
Figure 3:
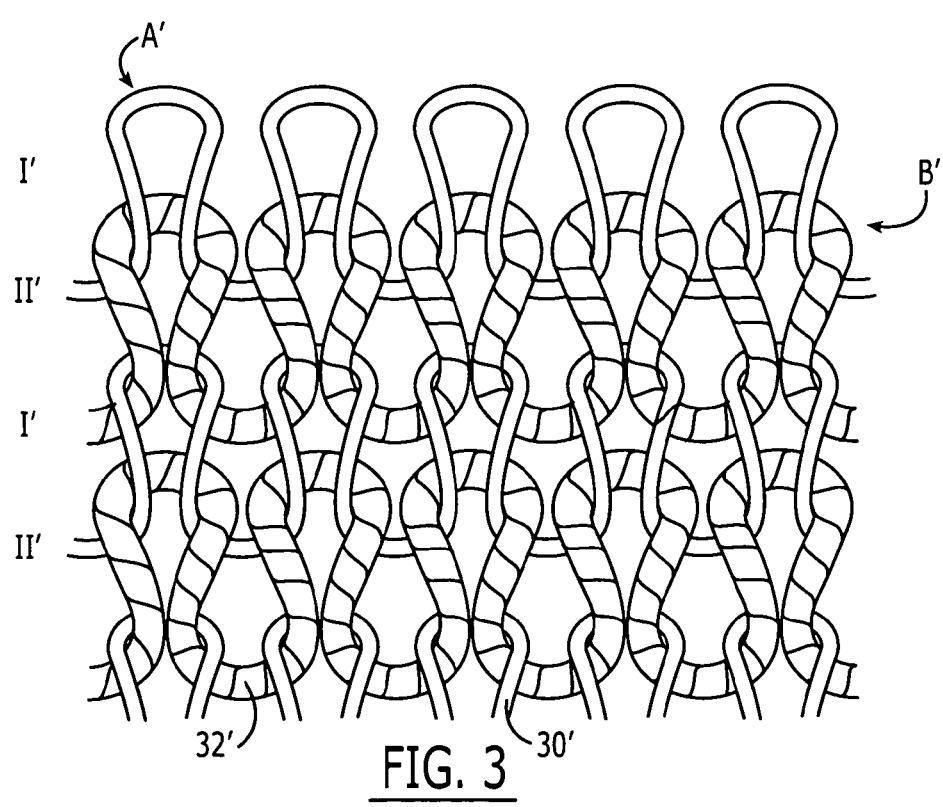

Having thus described the invention in general terms, reference will now be made to the accompanying drawings, which are not necessarily drawn to scale, and wherein:

FIG. 1 is a side elevation of an exemplary sock in accordance with the present invention;

FIG. 2 is an enlarged fragmentary view of a portion of the fabric enclosed by the circle 2 of FIG. 1 illustrating an enlarged detail of an exemplary open knit useful in a ventilation panel of the sock of the invention; and FIG. 3 is an enlarged fragmentary view of a portion of the fabric enclosed by the circle 3 of FIG. 1 illustrating an enlarged detail of an exemplary knit useful in a flex zone of the sock of the invention.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

As used in the specification, and in the appended claims, the singular forms "a", "an", and "the" include plural referents unless the context clearly dictates otherwise.

FIG. 1 is a side elevation of an exemplary sock in accordance with the present invention, designated generally at 10. Sock 10 includes a leg section 12 and a foot section 14. The sock of the invention can be produced using circular knitting machines as are known in the art.

Leg section 12 is formed of an elongate sleeve of textile material having sufficient expandability and/or stretchability to be easily drawn over at least a portion of the leg of the wearer between the ankle and the knee, and advantageously over substantially the entire portion of the calf of the leg of the wearer extending from the ankle to the knee. The material is also capable of resiliently engaging and covering at least a portion of the leg of the wearer of the sock. The invention, however, is not limited to a sock construction covering the calf of the wearer, and accordingly also includes sock constructions having a leg section capable of extending over the knee of the wearer and onto at least a part of the wearer's thigh. Alternatively, the sock of the invention can have a relatively shorter leg section, for example, a leg section that terminates just above the ankle.

The sleeve is formed of seamless expansion knit fabric, optionally with elastic yarn inlaid therein, having substantial circumferential expandability or stretchability. The expansion knit fabric can be, for example, a one-by one rib knit fabric as known in the art, in which a body yarn forms successive courses of stitch loops with the stitch loops in alternative wales facing outwardly and the stitch loops in intervening wales facing inwardly. An elastic yarn, such as a Lycra® yarn, can optionally pass alternatively in front of and behind adjacent stitch loops to provide additional circumferential expansion and/or stretchability.

The substantial expandability and/or stretchability of the leg section of the sock of the invention can provide several advantages over conventional sock constructions. As noted above, often diabetic or other patients with circulatory problems can exhibit substantial swelling in their extremities. Because the leg section of the sock of the invention is readily expanded, it can be readily fitted onto the wearer with relative ease and comfort. This can minimize irritation or discomfort, both when putting the sock on and during its use. The sock can also remain in place once fitted onto the wearer.

As used herein, the term "substantial circumferential expandability and/or stretchability" refers to the ability of the knit leg portion of the sock of the invention to be substantially expanded and/or stretched so that the outer circumference of the leg section is greater than the widest circumference of the leg of the wearer of the sock over which the sock is drawn. Advantageously, the leg portion of the sock has a circumferential expandability and/or stretchability sufficient to allow the circumference of the leg section to expand at least about twice, and up to three times, or more, its unstretched circumference. As non-limiting examples, the leg portion of the sock can have an initial unstretched circumference ranging from about three to about ten inches, which unstretched circumference can be expanded at least two times or more. One exemplary sock construction of the invention has an initial unstretched circumference of about eight inches and a stretched circumference of about twenty-six inches.

Foot section 14 of the sock 10 is dimensioned to fit over the foot of the wearer and extends generally from the heel to the toes. Foot section 14 includes an upper or instep section 18 located between a toe section 20 and a heel section 22. Foot section 14 also includes a lower or bottom sole section 16.

Instep section 18 includes along at least a portion thereof one or more ventilation panel(s), designated at 24' and 24", as described in more detail below. Instep section 18 further includes one or more flex zones 26, also as described in more detail below. Generally, ventilation panel(s) 24' and 24" provide desired air circulation and ventilation to the non-weight bearing portions of the foot. Flex zone 26 provides one or more regions which exhibit minimal bunching or wrinkling of the sock against the foot of the wearer, for example, when the foot bends in use. This advantageously minimizes irritation of the skin of the wearer.

Advantageously, at least one flex zone 26 is located along an upper portion of instep section 18 between an ankle portion 28 which covers the ankle joint of the wearer and ventilation panel 24". In one embodiment of the invention, as illustrated in FIG. 1, flex zone 26 is positioned between two sections of a ventilation panel. In this embodiment of the invention, flex zone 26 is integrally knit within the ventilation panel so as to divide the ventilation panel into two regions along the instep. The two ventilation regions are designated in FIG. 1 as upper ventilation panel 24', which is located along an upper portion of instep section 18 and is integrally knit to a lower end portion of leg section 12, and lower ventilation panel 24", which is located along a lower portion of instep section 18 adjacent toe section 20. In this embodiment of the invention, flex zone 26 is located along an intermediate portion of instep section 18 between ventilation panels 24' and 24".

The present invention is not limited to this particular arrangement of ventilation panel(s) and flex zones(s), and accordingly the sock of the invention can include one or more ventilation panels in combination with one or more flex zones at different locations of the instep section of the sock. As another non-limiting example, instep 18 can include a single flex zone integrally knit along an upper end thereof to the lower end of leg section 12 and integrally knit along a lower opposing end thereof to a ventilation panel. As another non-limiting example, instep section 18 can include more than one discrete flex zone, each of which is integrally knit into different regions of the ventilation panel of the instep section of the sock.

Ventilation panels 24' and 24" include an open or mesh knit construction. The open or mesh knit construction provides additional ventilation and air circulation for the wearer along at least a portion of a region of the foot where weight bearing cushioning is not required. Ventilation panels 24' and 24" thus include a knit construction that can allow a greater amount of air to pass therethrough as compared to the knit construction of other regions of the sock, and in particular as compared to flex zone 26.

The open or mesh knit construction of ventilation panels 24' and 24" can include tuck stitches interspersed with plain stitches. For example, the ventilation panel can include a pattern formed by alternating a plain stitch with a tuck stitch. The tuck stitches can be formed as known in the art by drawing one (or more) stitch loops and holding the stitch loop(s) on the needles while additional yarns are fed to the needle hook. These needles are not raised to shed level so that tuck loop(s) are formed and held in the hooks of the needles until the held loops and the tuck loops are shed from the needles with the formation of the next plain stitch loop(s).

The ventilation panel(s) can be knit using the yarns having the same properties. Advantageously, however, the ventilation panel(s) include two or more yarns having different properties, such as different deniers. For example, as illustrated in FIG. 2, the ventilation panel(s) advantageously include at least two yarns, designated generally at 30 and 32. In this aspect of the invention, yarn 30 has a smaller denier than yarn 32. Stated differently, yarn 32 is bulkier than yarn 30. As a non-limiting example, yarn 30 can have a denier of about 150 and yarn 32 can have a denier of about 540. The denier of each of the respective yarns, however, is not so limited and can be selected from a broad range of deniers useful in the production of knit socks, for example, deniers ranging from about 150 to about 600 denier, so long as yarns 30 and 32 have deniers that are different from one another. Deniers outside of this range can also be useful, again so long as yarns 30 and 32 have different deniers.

In addition, advantageously yarns 30 and 32 are formed of different materials. As a non-limiting example, advantageously the bulkier larger denier yarn 32 is an acrylic yarn. The smaller denier yarn can be formed of any of the types of material known of the art to be useful in the production of knit socks, which material can be selected based upon a particular desired property to be imparted to the ventilation panel(s). A particularly useful small denier yarn can be, for example, a nylon yarn. An elastic yarn, such as a Lycra® yarn, optionally can also be present in the ventilation panel(s), for example as a substitute for one of yarns 30 and 32 and/or as a separate yarn that passes alternatively in front of and behind adjacent stitch loops.

FIG. 2 illustrates an exemplary pattern of plain and tuck stitches useful in making the ventilation panel(s) of the sock of the invention. In this embodiment of the invention, the ventilation panel(s) include a four row or course repeat pattern as follows. Each row or course of the fabric includes stitches A, which includes yarn 30, alternating with stitches B, which include both of yarns 30 and 32. Stitch A results from tucking one of the yarns, here the larger denier yarn 32. This in turn can result in a more open knit.

The first two rows of the pattern (designated as I and II in FIG. 2) have the same pattern of alternating stitches A and B so that the stitches directly above one another in rows I and II are the same. The next two rows of the pattern (designated as III and IV in FIG. 2) include a pattern of alternating stitches A and B that are offset by one stitch relative to the pattern of stitches A and B in rows I and II. Similar to rows I and II, rows III and IV have the same pattern of alternating stitches A and B so that the stitches directly above one another in rows III and IV are the same. The present invention, however, is not limited to a particular pattern of plain and tuck stitches, such as that shown in FIG. 2, so long as the tuck stitches provide an open knit pattern suitable to provide the desired degree of ventilation and/or air circulation.

The width of the ventilation panel can vary to provide the desired degree of air circulation and ventilation for a particular application. Generally, ventilation panel(s) 24' and/or 24" extend from one side of the sock from the top of the sole section across the top of the foot to the opposite side of the sock to the sole section.

Flex zone 26 is constructed of a knit fabric designed to prevent substantial bunching or wrinkling of the sock against the foot of the wearer, for example, when the foot bends in use. Accordingly, flex zone 26 can be positioned along one or more regions of instep 18 where it is desired to reduce and/or eliminate wrinkling of the sock fabric, particularly as the foot moves. This, in turn, can help minimize and eliminate pressure points against the skin. Advantageously, the sock of the invention includes at least one flex zone located on an upper portion of the instep section below the leg section of the sock and between the ankle section and the ventilation panel. Additional flex zones, however, can also be present along the instep of the sock, as noted above.

To reduce wrinkling or bunching of the fabric, flex zone 26 is generally formed of a smaller or finer knit construction as compared to the knit structure of the ventilation panel. As such, the flex zone can be formed of a knit construction which includes a greater number of wales per inch as compared to the knit of the ventilation panel. The exact fineness of the flex zone can vary, depending upon the degree to which movement of the fabric is desirably restricted. Generally, the flex zone has a fineness ranging from about 10 to about 20 wales per inch, although values outside of this range can also be useful. The ventilation panel can have a fineness falling within this same range, e.g., from about 10 to about 20 wales per inch, so long as the fineness of the ventilation panel is less than the fineness of flex zone. The fineness of the flex zone can alternatively be defined in terms of the relative bulk of the yarns of various stitches of the flex zone, particularly as compared to the relative bulk of the yarns of various stitches of the ventilation panel(s), as discussed in more detail below.

Flex zone 26 also has a less open knit construction as compared to the knit construction of the ventilation panel, e.g., the flex zone generally does not include tuck stitches. The flex zone can be formed, for example, of a single knit or jersey knit pattern as is known in the art, such as that illustrated in FIG. 3, so long as the knit pattern has a fineness and/or openness selected to minimize or prevent wrinkling of the fabric.

Similar to the ventilation panel(s), while the flex zone can be knit using yarns having the same properties, advantageously the flex zone includes two or more yarns having different properties, such as different deniers. For example, as illustrated in FIG. 3, the flex zone advantageously include at least two yarns, designated generally at 30' and 32', which can be the same or different as yarns 30 and 32 of FIG. 2. In this aspect of the invention, yarn 30' has a smaller denier than yarn 32'. As a non-limiting example, yarn 30' can have a denier of about 150 and yarn 32' can have a denier of about 540. The denier of each of the respective yarns, however, is not so limited and can be selected from a broad range of deniers useful in the production of knit socks, for example, deniers ranging from about 100 to about 600 denier, so long as yarns 30' and 32' have deniers that are different from one another. Deniers outside of this range can also be useful, again so long as yarns 30' and 32' have different deniers.

In addition, also similar to the ventilation panel(s) of FIG. 2, advantageously yarns 30' and 32' are formed of different materials. As a non-limiting example, advantageously the larger denier yarn 32' is an acrylic yarn. The smaller denier yarn can be formed of any of the types of material as known of the art to be useful in the production of knit socks, which material can be selected based upon a particular desired property to be imparted to the flex zone. A particularly useful small denier yarn can be, for example, a nylon yarn. An elastic yarn, such as a Lycra® yarn, optionally can also be present in the flex zone, for example as a substitute for one of yarns 30' and 32' and/or as a separate yarn that passes alternatively in front of and behind adjacent stitch loops.

FIG. 3 illustrates an exemplary pattern of plain stitches useful in making the flex zone of the sock of the invention. In this embodiment of the invention, the flex zone includes a two row or course repeat pattern as follows. A first row (designated as I' in FIG. 3) includes stitches A' formed of less bulky yarn 30'. A second row (designated as II' in FIG. 3) includes stitches B' formed of bulkier yarn 32'. Rows I' and II' alternate with one another so as to provide a row of stitches A' formed of the less bulky yarn 30' alternating with a row of stitches B' formed of the bulkier yarn 32'. This pattern can be particularly useful in minimizing bunching of the flex zones as the foot moves. The present invention, however, is not limited to a particular pattern of plain stitches, such as that shown in FIG. 3, so long as knit of the flex zone minimizes bunching or wrinkling of the flex zone fabric as needed.

As noted above, the relative bulk of various stitches in the flex zone, particularly as compared to the relative bulk of stitches in the ventilation panel, can provide a finer knit for the flex zone. For example, while the same denier yarns can be used in both the ventilation panel and the flex zone, the resultant knit is bulkier in the ventilation panel due at least in part to the combination of both of yarns 30 and 32 in alternating stitches (stitch B).

The width of the flex zone can also vary, so long as the knit construction and placement along the instep is sufficient to provide the desired reduction of fabric bunching or wrinkling. Generally, flex zone 26 extends from one side of the sock from a region near the ankle section and along the top of the sole section across the top of the foot to the opposite side of the sock to the opposing ankle section and sole section.

Heel section 22 can be formed by any suitable technology. Advantageously, the heel section (or pocket) has a "Y heel" construction as known in the art. Alternatively, the sock can be configured so that the foot section 14 is a straight tubular structure without a heel pocket.

Toe section 20 can also be constructed using any of the techniques as known in the art. Toe section 20 can include one pocket for receiving all toes, or alternatively toe section 20 can include individual toe pockets, each configured to receive a corresponding one of the toes of the wearer. The circular knitting process generally used to manufacture the sock of the invention results in an opening adjacent toe section 20, and accordingly the sock of the invention advantageously further includes a closure seam 34. To form toe closure seam 34, opposing edges of the knit fabric structure are brought together and slightly superimposed or overlapped. The overlapping edges are then sewn together using a suitable yarn (which can be the same or different from the yarn used to knit the sock structure) in accordance with standard techniques known in the art for closing a knit sock toe opening. However, in contrast to conventional toe seam closures, closure seam 34 is preferably inverted or flat so that it is oriented outwardly and away from the skin of the wearer of the sock, e.g., the toe seam lies along an outer surface of the toe section of the sock so as to minimize frictional irritation of the skin.

Foot section 14 of sock 10 further includes a bottom or sole section 16. Sole 16 extends generally from the heel to the toe of the foot section. Sole 16 advantageously includes an integrally knit cushioning region which can have a greater thickness than adjacent regions to provide additional padding and protection for the wearer, and in particular for the weight bearing portions of the foot. The thicker padded regions of sole 16 can be formed using knitting techniques known in the art for knitting more yarn in a desired cushion region of the sole relative to the amount of yarn knitted into adjacent regions of the sock construction. As a non-limiting example, sole 16 can be formed using a sandwich plated cushion knit or sandwich terry knit as known in the art. In this embodiment of the invention, at least two yarns are knit one behind the other into the same loops. At least one of the yarns forms terry loops on a surface of the fabric. The sole section of the sock is knit so that the terry loops project inwardly toward the sole of the foot of the wearer.

The thicker padded region of sole 16 generally extends from the heel to the toe. The entire sole, however, is not required to be padded as described herein, and accordingly one or more discrete select regions of the sole can be padded.

The padded sole region can cushion the sole of the foot of the wearer to minimize irritation of the sole and thus to minimize and prevent blister formation and the like. The padded sole can also reduce impact forces to the foot of the wearer and increase comfort.

The sock of the invention can be produced using any of the types of yarns known in the art for the production of knit socks, including yarns made of synthetic and/or man-made fibers, natural fibers, and/or blends of the same. Exemplary synthetic fibers include without limitation acrylic fibers, polyolefin fibers, polyester fibers, polyamide fibers, and the like, as well as blends thereof with one another and/or with natural fibers. Exemplary natural fibers include without limitation cotton fibers, wool fibers, and the like, as well as blends thereof with one another and/or with synthetic fibers.

The various sections of the sock can be knit using the same or different yarns, and the type of yarn used to form a sock section can depend on the particular function of that given section of the sock. Acrylic yarn is particularly useful for knitting each of the sock sections because of its hydrophobic properties, which impart moisture wicking characteristics to the resultant sock to help keep the foot dry. Blends of acrylic yarns with one or more other yarns can also be useful, for example, to impart water absorption, durability, elasticity, and the like.

For example, as noted above, advantageously the leg section of the sock includes elastomeric yarn in combination with another yarn. The elastomeric yarn can be present in one or more of the other various regions or sections of the sock as well. Including elastomeric yarn in the leg section of the sock can provide stretchability as well as allow the leg section to resiliently engage the leg of the wearer and keep the leg section in place. Elastomeric yarns useful in the production of the socks of the invention are known in the art and include, for example, Lycra® yarns which are commercially available from DuPont.

The sock of the invention can include any of these types of yarns in conventional amounts. For example, the sock can include acrylic yarn in an amount ranging from about 85 to about 99% by weight, based on the total weight of the sock; an elastic yarn in an amount ranging from about 0.5 to about 5% by weight, based on the total weight of the sock; with the remainder of the sock comprising a yarn different from the acrylic and elastic yarn, such as a nylon yarn. One particularly useful sock of the invention includes about 90% by weight acrylic yarn; about 9.5% by weight nylon yarn; and about 0.5% by weight Lycra yarn.

The yarns used in making the sock of the invention advantageously also include an antimicrobial agent. The antimicrobial agent is selected to minimize and/or prevent growth of bacteria and fungi on the sock and to minimize and/or eliminate odors. Useful antimicrobial agents are known on the art and are commercially available.

In the drawings and specification there has been set forth a preferred embodiment of the invention, and although specific terms have been employed, they are used in a generic and descriptive sense only and not for purposes of limitation, the scope of the invention being defined in the claims.

What is claimed is:

1. A knit sock useful for patients susceptible to foot problems, comprising:
   a leg section having sufficient expandability to be drawn over and cover at least a portion of a leg of a wearer; and
   a foot section comprising a heel section, a toe section, a sole section, and an instep section, wherein the instep section comprises at least one ventilation panel having a first knit construction to allow the passage of air therethrough and to provide ventilation along at least a portion thereof and wherein the instep section further comprises at least one flex zone having a second knit construction that is different from the first knit construction of the ventilation panel to prevent bunching of the sock against the foot of the wearer as the foot bends in use.

2. The sock of claim 1, wherein said at least one ventilation panel is located between the toe section and an ankle section of the sock covering an ankle joint of the wearer.

3. The sock of claim 2, wherein said at least one flex zone is located on an upper portion of the instep section between the ankle section and the ventilation panel.

4. The sock of claim 3, wherein said at least one flex zone extends from one side of the sock from a region near the ankle section across the top of the foot to the opposite side of the sock to the opposing ankle section.

5. The sock of claim 3, wherein said at least one flex zone is integrally knit to a lower portion of the leg section.

6. A knit sock useful for patients susceptible to foot problems, comprising:
   a leg section having sufficient expandability to be drawn over and cover at least a portion of a leg of a wearer; and
   a foot section comprising a heel section, a toe section, a sole section, and an instep section,
   wherein the instep section comprises at least a first and a second ventilation panel between the toe section and an ankle section of the sock covering an ankle joint of the wearer, each having a first knit construction to allow the passage of air therethrough and to provide ventilation along at least a portion thereof, wherein the first ventilation panel is located along an upper portion of the instep section integrally knit to a lower portion of the leg section; the second ventilation panel is located along a lower portion of the instep section; and
   wherein the instep section further comprises at least one flex zone located along an intermediate portion of the instep section between the first and second ventilation panels having a second knit construction that is different from the first knit construction of the ventilation panels to prevent bunching of the sock against the foot of the wearer as the foot bends in use.

7. The sock of claim 1, wherein said at least one ventilation panel comprises a knit construction that is more open than the knit construction of said at least one flex zone.

8. The sock of claim 1, wherein said at least one ventilation panel has an open stitch construction.

9. The sock of claim 8, wherein said at least one ventilation panel comprises tuck stitches interspersed with plain stitches.

10. A knit sock useful for patients susceptible to foot problems, comprising:
  a leg section having sufficient expandability to be drawn over and cover at least a portion of a leg of a wearer; and
  a foot section comprising a heel section, a toe section, a sole section, and an instep section, wherein the instep section comprises at least one ventilation panel having a first knit construction to allow the passage of air therethrough and to provide ventilation along at least a portion thereof and wherein the instep section further comprises at least one flex region having a second knit construction that is different from the first knit construction of the ventilation panel to prevent bunching of the sock against the foot of the wearer as the foot bends in use, wherein said ventilation panel comprises a first yarn having a first denier and a second yarn having a second denier that is smaller than the denier of said first yarn.

11. The sock of claim 10, wherein said first and second yarns are formed of different materials.

12. The sock of claim 11, wherein said first yarn having a larger denier is an acrylic yarn.

13. The sock of claim 12, wherein said second yarn having a smaller denier is a nylon yarn.

14. The sock of claim 10, wherein said ventilation panel comprises a plurality of rows comprising a plurality of stitches A formed of said second yarn having a smaller denier alternating with a plurality of stitches B formed of a combination of said first yarn having a larger denier and said second yarn having a smaller denier.

15. The sock of claim 14, wherein said ventilation panel comprises a four row repeat pattern, wherein the first and second rows of said four row repeat pattern comprise the same pattern of alternating stitches A and B so that the stitches directly above one another in said first and second rows are the same, and wherein the third and fourth rows of said four row repeat pattern comprise a pattern of alternating stitches A and B that is offset by one stitch relative to the pattern of stitches A and B of said first and second rows, and further wherein said third and fourth rows comprise the same pattern of alternating stitches A and B so that the stitches directly above one another in said third and fourth rows are the same.

16. The sock of claim 1, wherein said at least one flex zone has a jersey knit construction.

17. The sock of claim 1, wherein said at least one flex zone comprises a finer knit construction as compared to the knit construction of said at least one ventilation zone.

18. A knit sock useful for patients susceptible to foot problems, comprising:
  a leg section having sufficient expandability to be drawn over and cover at least a portion of a leg of a wearer; and
  a foot section comprising heel section, a toe section, a sole section, and an instep section, wherein the instep section comprises at least one ventilation panel having a first knit construction to allow the massage of air therethrough, and to provide ventilation along at least a portion thereof and wherein the instep section further comprises at least one flex region having a jersey knit construction that is different from the first knit construction of the ventilation panel to prevent bunching of the sock against the foot of the wearer as the foot bends in use, wherein said flex zone comprises a first yarn having a first denier and a second yarn having a second denier that is smaller than the denier of said first yarn.

19. The sock of claim 18, wherein said first and second yarns are formed of different materials.

20. The sock of claim 18, wherein said first yarn having a larger denier is an acrylic yarn.

21. The sock of claim 20, wherein said second yarn having a smaller denier is a nylon yarn.

22. The sock of claim 18, wherein said flex zone comprises a plurality of rows comprising stitches formed of said first yarn having a larger denier alternating with a plurality rows comprising stitches formed of said second yarn having a smaller denier.

23. The sock of claim 1, wherein the leg section comprises a rib knit construction.

24. The sock of claim 23, wherein the leg section comprises an elastic yarn.

25. The sock of claim 1, wherein the toe section comprises an inverted toe closure seam oriented outwardly away from a surface of the sock contacting the skin of a wearer.

26. The sock of claim 1, wherein the sole section comprises an integrally knit cushioning region to provide additional padding and protection for the wearer.

27. The sock of claim 26, wherein the sole section comprises a sandwich plated cushion knit comprising a plurality of terry loops on a surface of the sole section adjacent the foot of the wearer.

28. The sock of claim 1, wherein the heel section comprises a Y heel construction.

29. The sock of claim 1, wherein the sock comprises one or more yarns comprising synthetic fibers, natural fibers, or a blend of synthetic fibers and natural fibers.

30. The sock of claim 29, wherein said one or more yarns comprise fibers having moisture wicking properties.

31. The sock of claim 30, wherein said one or more yarns comprise acrylic fibers.

32. A knit sock useful for patients susceptible to foot problems, comprising:
  a leg section having sufficient expandability to be drawn over and cover at least a portion of a leg of a wearer; and
  a foot section comprising a heel section, a toe section, a sole section, and an instep section, wherein the instep section comprises at least one ventilation panel located between the toe section and an ankle section of the sock covering an ankle joint of the wearer and having an open knit construction to allow the passage of air therethrough and to provide ventilation along at least a portion thereof, and wherein the instep section further comprises at least one flex zone located on an upper portion of the instep section between the ankle section and the ventilation panel and extending from one side of the sock from a region near the ankle section across the top of the foot to the opposite side of the sock to the opposing ankle section and having a second finer knit construction as compared to the first knit construction of the ventilation panel, to prevent bunching of the sock against the foot of the wearer as the foot bends in use.

33. The sock of claim 32, wherein the sole section comprises a sandwich plated cushion knit comprising a plurality of terry loops on a surface of the sole section adjacent the foot of the wearer to provide additional padding and protection for the wearer.

34. The sock of claim 33, wherein the toe section comprises an inverted toe closure seam oriented outwardly away from a surface of the sock contacting the skin of a wearer.

35. The sock of claim 24, wherein the leg section comprises a rib knit construction having an elastic yarn laid therein.

36. The sock of claim 35, wherein the leg section has substantial circumferential expandability.

37. The sock of claim 36, wherein the leg section has a circumferential expandability sufficient to allow the circumference of the leg section to expand at least about twice its unstretched circumference.

* * * * *